United States Patent [19]

Behrmann et al.

[11] Patent Number: 5,168,091

[45] Date of Patent: Dec. 1, 1992

[54] ACTIVATION CONDITIONS TO MAXIMIZE THE HSC ACTIVITY OF SUPPORTED COBALT CATALYSTS

[75] Inventors: William C. Behrmann; Stephen M. Davis; Charles H. Mauldin, all of Baton Rouge, La.

[73] Assignee: Exxon Research and Engineering Company, Florham Park, N.J.

[21] Appl. No.: 770,077

[22] Filed: Sep. 30, 1991

Related U.S. Application Data

[63] Continuation-in-part of Ser. No. 597,988, Oct. 15, 1990, abandoned.

[51] Int. Cl.⁵ .................. B01J 37/18; B01J 23/74; B01J 23/76; B01J 23/84
[52] U.S. Cl. .................................... 502/325
[58] Field of Search .............................. 502/325

[56] References Cited

U.S. PATENT DOCUMENTS

| | | | |
|---|---|---|---|
| 4,302,359 | 11/1981 | Mauldin et al. | 502/331 |
| 4,568,663 | 2/1986 | Mauldin | 502/325 |
| 4,605,676 | 8/1986 | Kobylinski et al. | 502/335 X |
| 4,605,679 | 8/1986 | Kobylinski et al. | 502/332 X |
| 4,801,573 | 1/1989 | Eri et al. | 502/304 X |
| 4,826,800 | 5/1989 | McAteer | 502/304 x |
| 4,880,763 | 11/1989 | Eri et al. | 502/304 X |
| 4,962,078 | 10/1990 | Behrmann et al. | 502/325 |

FOREIGN PATENT DOCUMENTS

| | | | |
|---|---|---|---|
| 0168894 | 1/1986 | European Pat. Off. | 502/325 |
| 0253924 | 1/1988 | European Pat. Off. | 502/325 |
| 0266898 | 5/1988 | European Pat. Off. | 502/325 |
| 2153250 | 8/1985 | United Kingdom | 502/325 |

*Primary Examiner*—W. J. Shine
*Assistant Examiner*—Douglas J. McGinty
*Attorney, Agent, or Firm*—Jay Simon

[57] ABSTRACT

The activity of supported cobalt catalysts for hydrocarbon synthesis is maximized by carrying out the reduction at conditions that keep both the partial pressure of water vapor and the maximum reduction temperature below critical maximum values. For titania supported cobalt catalysts, the preferred maximum water partial pressure is one atmosphere and the preferred maximum reduction temperature is 375° C.

15 Claims, 4 Drawing Sheets

ACTIVATION CONDITIONS TO MAXIMIZE THE HSC ACTIVITY OF SUPPORTED COBALT CATALYSTS

CROSS REFERENCE TO RELATED APPLICATION

This is a continuation-in-part application of U.S. Ser. No. 597,988, filed Oct. 15, 1990, now abandoned.

FIELD OF THE INVENTION

This invention relates to activating cobalt containing hydrocarbon synthesis catalysts. More particularly, this invention relates to maximizing hydrocarbon synthesis catalyst activity by controlling the temperature in the activation step and by controlling the maximum water partial pressure produced during the activation step. Still more particularly, this invention relates to reducing a reducible cobalt compound, that produces water during reduction, to a catalytically active state under conditions that limit the water partial pressure produced during the reduction step.

BACKGROUND OF THE INVENTION

The activation of hydrocarbon synthesis catalysts is widely reported in the literature. Activation usually involves reduction, in a flowing hydrogen or hydrogen containing gas stream, at elevated temperatures. The reduction proceeds from a reducible metal compound, usually, but not necessarily the metal oxide. Thus, the literature reports reduction of metal oxides to the elemental or active form of the metal as well as reduction from metal compounds, impregnated either as water soluble or hydrocarbon soluble salts.

For example, hydrocarbon synthesis catalysts are usually prepared by depositing a metal, such as cobalt or other Group VIII metals onto a support, by techniques such as impregnation, the metal being in a water soluble (e.g., cobalt nitrate) or hydrocarbon soluble (e.g., cobalt carbonyl) form. The catalyst is usually dried to eliminate the solvent, but reduction (or activation) does not occur during the drying step even though a hydrogen containing gas may be used as the drying agent.

Once having the metal compound impregnated onto the support, activation by reducing t o the elemental or catalytically active form of the metal may proceed directly from the metal compound, or the metal compound may be converted to a more easily reducible form, such as the oxide and then reduced to its elemental or catalytically active form. In either case the metal compound must be reducible to its catalytically active form; the oxide is one form of reducible metal compound.

U.S. Pat. No. 4,605,676, shows the activation of cobalt containing hydrocarbon synthesis catalysts wherein the activation steps, including oxidation and reduction, are all carried out at temperatures between about 100° C. and 450° C. U.S. Pat. Nos. 4,670,675 and 4,605,679 also show activation procedures wherein cobalt containing catalysts are reduced at temperatures below about 500° C. These patents, however, do not recognize the effect of water partial pressure when water is produced during the reduction (or activation) step. Thus, this invention recognizes that temperature of reduction, by itself, does not fully account for differences in hydrocarbon synthesis catalyst activity.

Additionally, the aforementioned patents as well as U.S. Pat. No. 4,801,573, conduct the reduction step at ambient conditions, that is, one atmosphere, and the water partial pressure will necessarily be quite low. Obviously, the water partial pressure cannot be greater than the total pressure of the system. These reducing steps reflect laboratory experiments and are representative of gross effects such as oxidation or reduction. Nevertheless, large scale or commercial operations necessarily involve reducing the metal compound at elevated pressures because of pressure drop considerations in large-scale equipment.

Recently allowed European patent 0168894B1 discloses an activation process wherein the hydrogen partial pressure during catalyst activation is gradually raised to a value at least five times the initial hydrogen partial pressure at treatment temperatures of 200°–350° C. The total pressure during catalyst activation never exceeded 2 bar. Such conditions do not even approach the conditions at which commercial activation procedures take place, and consequently, do not afford a situation where the effects of water partial pressure can be determined.

Consequently, laboratory scale experiments at atmospheric or relatively low pressures can provide no guidance for water partial pressure effects at elevated pressures. Furthermore, at ambient conditions, problems in catalyst activity due to water partial pressure effects will not be recognizable since at total pressures of one or two atmospheres water partial pressure does not present a problem. Further, the recognition of water partial pressure as an important element in hydrocarbon synthesis catalyst activation has never before been recognized.

One object of this invention, therefore, is providing a method for activating hydrocarbon synthesis catalysts at pressures indicative of commercial operation and greater than atmospheric pressure. Another object of this invention is providing a procedure for determining the water partial pressure by determining the factors that affect water pressure. This procedure allows the prediction of water partial pressure under a variety of interdependent variables, and therefore, allows the predetermination of a number of different conditions that allow an operator to maximize hydrocarbon synthesis catalyst activity.

SUMMARY OF THE INVENTION

In accordance with this invention, a highly active hydrocarbon synthesis catalyst is prepared by reducing a metal compound, at elevated temperatures and pressures and in the presence of a hydrogen containing gas stream, to its catalytically active form while maintaining the total pressure at 1.3–10 atmospheres, preferably 2–4 atmospheres, and the water partial pressure during the reduction at less than about five atmospheres, preferably 0.1 to 5 atmospheres, more preferably 0.1–2.0 atmospheres and still more preferably 0.2–0.8 atmospheres. Operating at lower water partial pressures does not improve the activity of the resulting catalyst and may be very difficult and expensive to accomplish. In a preferred embodiment, the reduction step, which is the catalyst activation step, is carried out below about 550° C., and preferably in the range of about 250°–425° C.

While water vapor can be introduced into the reduction step with the hydrogen containing gas, either on purpose as steam or as a contaminant, the bulk of the water vapor comes from the metal compound being reduced, usually an oxygen containing compound, the most common compound being the metal oxide form.

In another embodiment of this invention the variables affecting water partial pressure during the reducing or activating step have been identified, and therefore, a determination of the water partial pressure can be made beforehand and a catalyst of high activity produced. These factors are: weight percent of the metal compound, hydrogen containing gas flow rate and water content thereof, rate of temperature rise during the reducing/activating step, total pressure and hydrogen partial pressure, and reactor type.

Thus, the activation procedure is not dependent on the particular support or particular structural promoter employed, and this invention is applicable to the use of any support or structural promoter generally used in the preparation of hydrocarbon synthesis catalysts. For example, inorganic oxides, particularly difficultly reducible, inorganic oxides selected from the metals of Groups III-VI of the Periodic Chart of the Elements are often used as supports for hydrocarbon synthesis catalysts, and they may be used in the method of this invention. Additionally, structural promoters employed in the preparation of catalysts by micelle technology wherein the structural promoter may be similar to materials used as supports but act instead as providing a structure for the catalytic metal (the catalytic metal and the material being composited as an aggregate rather than the material supporting the catalytic metal). A detailed description of micelles is provided in the Encyclopedia of Science and Technology, 6th Ed., McGraw-Hill publisher, New York 1987, and in Preparation of Catalysts IV by Ravet et al, 505-507, Delmon, Grange, Jacobs, and Poncelet Eds., Elsevier, 1987.

DETAILED DESCRIPTION OF THE INVENTION

Figure 1:
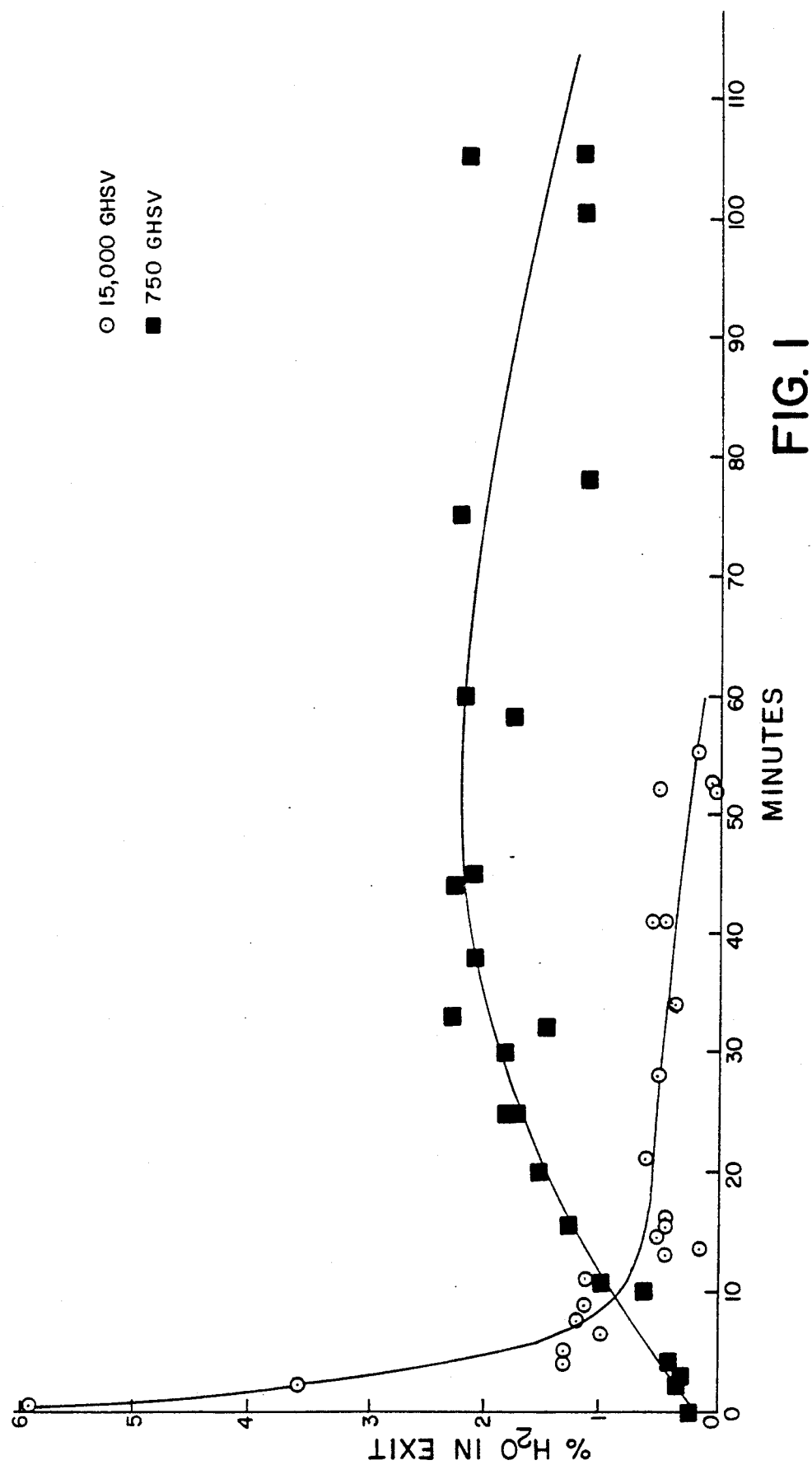
FIG. 1 is a plot of percent $H_2O$ in the exit gas v. time for two different hydrogen reduction flow rates at 450° C., 100 psig for Catalyst A.

Hydrocarbon synthesis catalysts are generally prepared by depositing a catalytic metal, usually cobalt, upon a suitable support, e.g., a difficultly reducible, porous, inorganic oxide, usually by contacting the support by any of a number of known methods, with a salt of cobalt. During the contacting step the cobalt salt is impregnated onto the support. After impregnation, the supported catalyst precursor is dried to eliminate any excess solvent, that is, water by virtue of using water soluble salts, or hydrocarbon solvent by virtue of using hydrocarbon soluble compounds. Drying can be accomplished with mild heating, up to about 125° C. in the presence of flowing gas containing oxygen or hydrogen, either being optionally diluted with an inert gas. When the drying gas contains hydrogen, reduction does not occur at normal drying temperatures and at the worst any reduction that does occur will be insubstantial.

In some instances drying and reducing/activating are accomplished in a single step by simply raising the temperature when drying is substantially complete. Nevertheless, at the onset of reduction, whether one step drying/reducing or two step drying and reducing is employed the catalyst precursor comprises a reducible cobalt compound that forms water during reduction of the precursor with hydrogen. A preferred reducible cobalt compound is the oxide which is prepared by treating the cobalt salt with an oxygen containing gas, e.g., air, at temperatures of about 150° C. to about 550° C. for a period sufficient to convert all or substantially all of the salt to the oxide.

Since the factors determining water partial pressure during reducing/activating do not include the nature of the support, this invention is applicable, generally, to any of the known catalyst supports. Nevertheless, the support itself should be free of water or water precursors to the extent that when heated the support generates essentially no water vapor. Typical supports include the oxides of metals of Groups IIIA, IIIB, IVB, VB, VIB, VIIIB, mixtures thereof, and mixtures thereof with other metal oxides, e.g., alkali, alkaline earth metal oxides or rare earth metal oxides. Preferred supports are those of lower surface area, e.g., less than about 100 $m^2/gm$, preferably less than about 75 $m^2/gm$. Preferred materials are the Group IVB metal oxides: zirconia, hafnia, and titania as well as lower surface area aluminas, silicas and silica-aluminas. Particularly preferred are the Group IVB oxides, specifically titania, or a support containing at least about 50 wt% titania, more preferably at least about 80 wt% titania.

When employing titania or a titania containing support, the rutile:anatase ratio is at least 2:3 as determined by x-ray diffraction (ASTM D 3720-78). Preferably, the rutile:anatase ratio is at least about 3:2, more preferably at least about 4:1, an all rutile titania is most preferred since high rutile content titania provides a support wherein optional activity to heavy hydrocarbons, e.g., $C_{10}+$, without significant gas make, can be obtained.

The hydrocarbon synthesis catalyst is activated by reduction, which is carried out with hydrogen or a hydrogen containing gas. The gas may be diluted with an inert such as nitrogen, helium, or argon. Other materials often considered inert such as CO or $CO_2$ are not inert at these conditions and may either be hydrogenated or result in carbon formation on the catalyst.

In accordance with this invention, we have found that the final temperature of the reduction has a significant effect on the ultimate hydrocarbon synthesis activity of the catalyst. In a preferred embodiment of this invention, substantially complete reduction is effected at temperatures below about 550° C., preferably from about 275° C. to about 425° C. and most preferably, for maximizing catalytic activity, reduction is effected at temperatures ranging from 315° C. to about 375° C.

Temperature effects appear to be reversible, whereas water partial pressure effects are apparently irreversible. That is, incomplete reduction at relatively low temperatures or over reductions at relatively high temperatures, both of which lead to poor catalytic activity, can be cured and catalyst activity restored by, e.g., a 250° C. air treat followed by a satisfactory reduction step. Poor activity due to poor control of the water partial pressure during reduction cannot, however, be cured in this manner. The exact mechanism affecting catalytic activity by virtue of water partial pressures effects is unknown, nevertheless, the effect is clearly recognizable and can be substantially eliminated by controlling the water partial pressure during reduction.

Reduction temperatures above 550° C. are generally not employed for reducing cobalt compounds because of deleterious effects on catalytic activity. Additionally, increasing the reduction temperature has the effect of either causing the cobalt to agglomerate or resulting in an SMSI (strong metal-support interaction) effect which causes a support overlayer to form over the cobalt. In either case, the effective cobalt surface area is significantly reduced and hydrocarbon synthesis catalyst activity is deleteriously affected. On the low end of the temperature scale, the cobalt compound must be substantially reduced to obtain the catalytically active form and thereby achieve reasonable catalytic activity.

Figure 3:
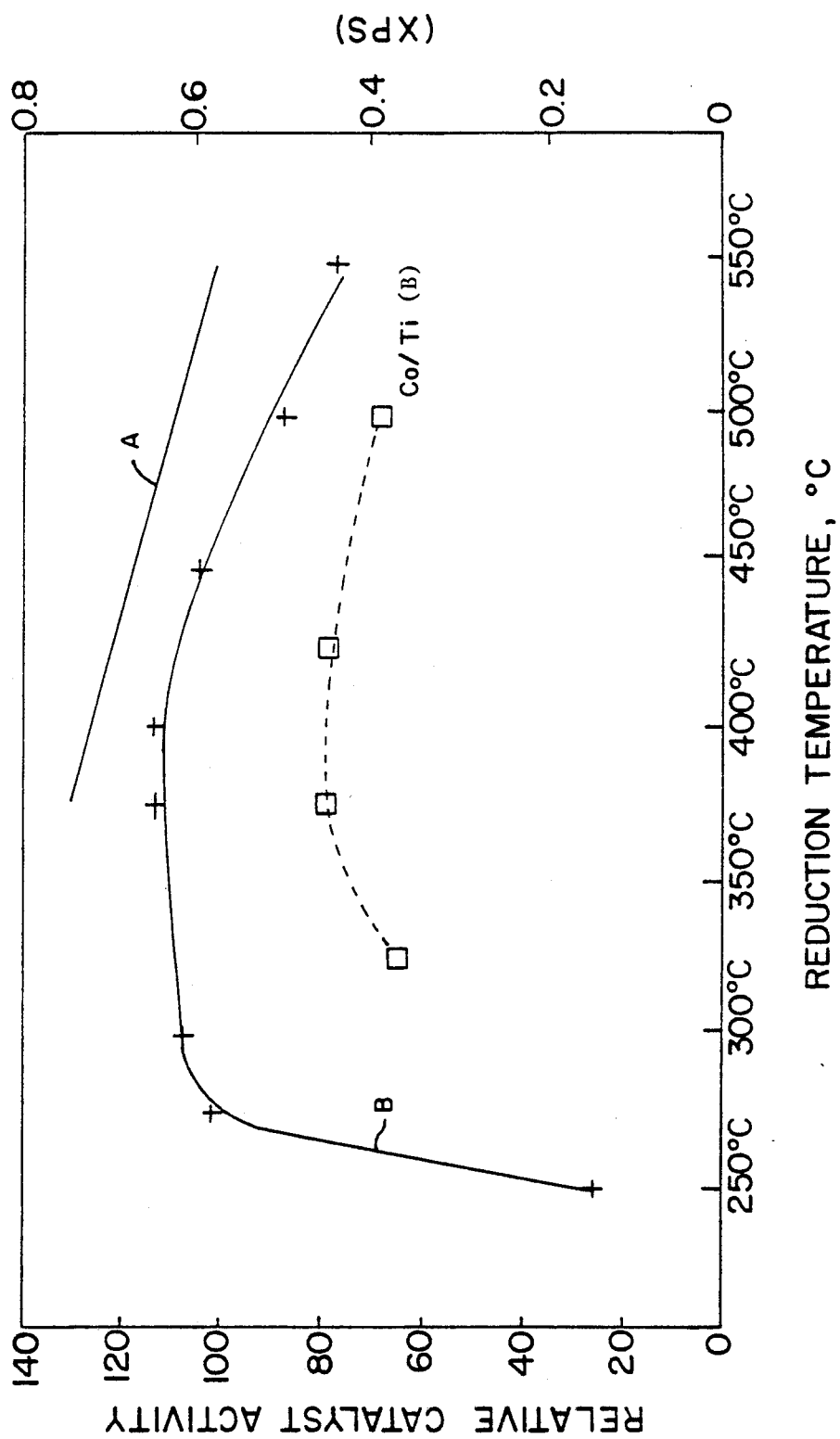
FIG. 3 is a plot of relative catalyst activity v. maximum reduction temperature for Catalysts A and B. XPS signal ratio for Catalyst B v. maximum reduction temperature is also shown. Water partial pressure was less than 0.24 atm during these tests.

Referring to FIG. 3, maximum reduction temperature is plotted against relative catalyst activity for catalyst B. Maximum activity increases sharply at reduction temperatures of about 260° C. and is likely due to overcoming the reducing threshold of the cobalt compound. Activity remains high and starts to decrease at temperatures of about 400° C. and more so above about 425° C. These results were obtained at a maximum water partial pressure of 0.24 atmospheres and, therefore, represent maximum relative activity for this particular catalyst.

The results for catalyst A are also plotted in FIG. 3 and show a decrease in relative catalytic activity at reduction temperatures above about 370° C.

Also shown in FIG. 3 is the XPS signal from the catalyst surface. As the reduction temperature increases above about 370° C. for Catalyst B, the cobalt signal declines relative to th titania signal suggesting either that the cobalt is agglomerating or that a titania overlayer is beginning to form on the cobalt crystallites (a typical SMSI phenomenon). Either mechanism results in reducing the exposed metal surface area which is the parameter directly responsible for catalytic activity.

Figure 2A:
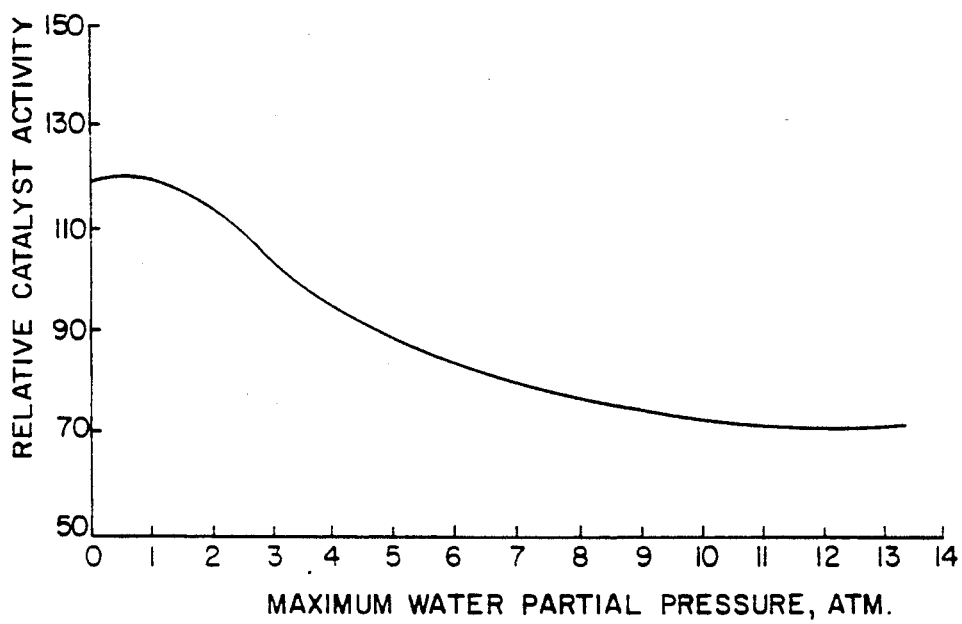
FIG. 2a is a plot of relative catalyst activity at 200° C. v. maximum water partial pressure in atmospheres, for reduction in hydrogen with temperature ramped from ambient to a maximum of 450° C. for Catalyst A.

The second and more important factor in the reduction step which has a significant effect on the ultimate activity of the catalyst is the maximum water partial pressure. Water is formed by the reduction reaction and can build up to significant partial pressures, depending on several factors. In accordance with this invention, the water partial pressure is controlled to ensure optimum activity. FIG. 2a shows that water partial pressures during reduction of greater than about 9 atmospheres cause a low activity, i.e., the curve becomes either flat or asymptotic at relative activity levels of about 70. In order to maintain high catalyst activity levels, water partial pressure should range from about 0.1–5 atmospheres. Stated another way, water partial pressure levels during reduction should be maintained at levels that furnish at least about 75% of maximum relative catalyst activity, preferably at least about 90% of maximum relative activity. In this manner, regardless of the maximum catalyst activity, which occurs at water partial pressures of about, e.g., 0.1–2.0 atmospheres the maximum water partial pressure that allows a certain level of catalyst activity can be predetermined.

The catalyst of this invention is useful in hydrocarbon synthesis reactions, that is, the catalytic conversion of synthesis gas, hydrogen and carbon monoxide, to higher hydrocarbons, preferably $C_5+$ hydrocarbons. The hydrocarbon synthesis process is carried out at temperatures of about 160° C. to 325° C., preferably 190° C. to 260° C., pressures of 5 atm to 100 atm (which also covers the activation pressures), preferably about 10–40 atm and gas hourly space velocities of 100 V/hr/V to 5000 V/hr/V, preferably 300 V/hr/V to 1500 V/hr/V. The stoichiometric ratio of hydrogen to carbon monoxide in the synthesis gas is about 2.1/1 for the production of higher hydrocarbons. However, $H_2/CO$ ratios of 1/1 to about 4/1, preferably about 1.5/1 to about 2.5/1, more preferably about 1.8/1 to 2.2/1 can be employed. These reaction conditions are well known and particular reaction conditions will be determined easily by those skilled in the art. Also, the reaction may occur in any type reactor, e.g., fixed bed, fluidized bed, slurry bubble column, etc.

The catalysts employed in the practice of this invention may be prepared by techniques known in the art for the preparation of hydrocarbon synthesis catalysts. The catalyst can, e.g., be prepared by gellation, or cogellation techniques. Suitably however the metals can be deposited on a previously pilled, pelleted, beaded, extruded, or sieved support material by the impregnation method. In preparing catalysts, the metals are deposited from solution on the support in preselected amounts to provide the desired absolute amounts, and weight ratio of the metal or metals being deposited. Suitably, cobalt by itself or with a promoter are composited with the support by contacting the support with a solution of a cobalt-containing compound, or salt, or a promoter-containing compound, or salt. Optionally, the cobalt and promoter can be co-impregnated upon the support. The cobalt and promoter compounds used in the impregnation can be any organometallic or inorganic compounds which when reduced in hydrogen form water or which can be converted to the corresponding oxide, which when reduced in hydrogen forms water., such as a cobalt or promoter, nitrate, acetate, acetylacetonate, naphthenate, or the like. The nitrate is preferred for cobalt. The amount of impregnation solution used should be sufficient to completely immerse the carrier, usually within the range from about 1 to 20 times of the carrier by volume, depending on the metal, or metals concentration in the impregnation solution. The impregnation treatment can be carried out under a wide range of conditions including ambient or elevated temperatures.

Promoter materials, such as rhenium, cerium, hafnium, and uranium can be included in the catalyst. Usually, these materials are present in a weight ratio to cobalt of at least about 0.05:1, preferably at least about 0.1:1 and may range from about 0.1:1 to 1:1, but the promoter is usually present in an amount less than the cobalt. Rhenium is a particularly preferred promoter and may be deposited onto the support as perrhenic acid. The amount of cobalt employed is at least that which is catalytically effective, e.g., at least about 2 wt%. However, cobalt concentrations may range from about 2–35 wt%, preferably 5–25 wt%.

The cobalt and promoter, e.g., rhenium, may be added serially although it is preferred to have the rhenium on the support before the cobalt is calcined. Or the metals may be simutaneously deposited onto the support.

In a preferred method for preparing the catalyst, cobalt or cobalt and one or more additional metals is deposited as a catalytically active layer, upon the peripheral or outside layer of a particulate porous inorganic oxide support by contacting the support and impregnating it with a liquid, suitably a suspension or solution, of a compound of said metal, or metals, while the support particles are in a fluidized bed maintained at a temperature above about 50° C., preferably at a temperature ranging from about 50° C. to about 100° C., and more preferably from about 70° C. to about 90° C. The catalytically active surface layer, ranges in average thickness from about 10 microns to about 250 microns, preferably from about 20 microns to about 200 microns, with the loading of the cobalt expressed as the weight metallic cobalt per packed bulk volume of catalyst ranging from at least about 0.04 grams per cubic centimeter preferably from about 0.05 g/cc to about 0.25 g/cc catalyst.

One preferred method for preparing catalysts, either powdered or with particle size up to 3 or 4 mm is disclosed in Preparation of Highly Selective and Abrasion-Consistant Thick Shell Catalysts for Heterogeneously Catalyzed Exothermic Oxidation Reactions, Arntz, D. and Prescher, G., Preparation of Catalysts IV, Elsevier, Amsterdam, The Netherlands, p. 137-147 (1987).

The catalyst, after metal deposition, e.g., impregnation, is dried by heating at a temperature above about 30° C., preferably between 30° C. and 125° C., in the presence of nitrogen, oxygen, hydrogen, or air, in a gas stream or under vacuum. Subsequent to drying the metal or metals may be converted to the oxide form and then reduced/activated with a hydrogen or hydrogen containing gas stream or the metal or metals may be reduced/activated directly and the oxide formation is eliminated. Preferably, however, the catalyst is activated by reduction from the oxide form. Conversion to the oxide takes place in air or an oxygen containing stream at temperatures above about 150° C., preferably in the range 150°–550° C., more preferably about 150° to 300° C.

Reduction/activation of the catalyst is effected in hydrogen or a hydrogen containing gas stream at temperatures above about 250° C., preferably from about 250° C. to about 550° C., and more preferably from about 275° C. to about 425° C., for periods ranging from about 0.5 to about 24 hours and at pressures ranging from above ambient to about 40 atmospheres.

Reactor vessels should be selected that avoid excessive buildup of water vapor. Thus, fluid beds are generally preferred where the hydrogen containing reducing gas fluidizes the catalyst particles. Reactors with high L/D ratios should be avoided.

Water partial pressure can be determined by direct measurement with available analytical devices, such as Drager tubes or suitable water analyzers manufactured for example by Manufacturers Engineering and Equipment Corp., Warrington, PA., or by calculation. In calculating water partial pressure, the factors that affect water partial pressure are: total pressure; hydrogen and water concentrations in the reducing gas; total gas rate, e.g., space velocity; reactor type; rate of temperature increase, e.g., the ramp schedule; metal compound concentration.

Determination of water vapor partial pressure can be made by means of a model wherein the first consideration is the material balance for water vapor, which for any given (or predetermined) volume element of a reactor for a given (or predetermined) time period is expressed as (moles H$_2$O flowing into the volume element)+(moles water produced by reduction)=(moles water flowing out of the volume element)+(moles water accumulated in the volume element).

The material balance expression is easily formulated and solved for the particular reaction vessel being used.

This invention focuses on the moles of water produced by reduction in the volume element per unit time. For example, a hydrocarbon synthesis catalyst precursor containing cobalt oxide on a rutile titania support, gives rise to the following kinetic expressions to describe the rate at which water is produced in gram moles/minute/cc volume of reactor:

$$\frac{(\rho_{cat})(Co)(4)}{(3)(58.93)} \left( (0.25)\frac{d(y)_1}{dt} + 0.75\frac{d(y)_2}{dt} \right)$$

in which $\rho_{cat}$ is the catalyst bulk density, gm/cc

Co is the weight fraction cobalt on dried, oxidized catalyst $$\frac{d(y)_1}{dt}$$

is the reduction rate of Co$_3$O$_4$ to CoO $$\frac{d(y)_2}{dt}$$

is the reduction rate of CoO to metallic cobalt

The individual reaction rates can be further expressed for the reduction of Co$_3$O$_4$ to CoO:

$$\frac{d(y_1)}{dt} = (A_1)(F(Y_1))(F(T_1))(F(P_{H2}))(F(P_{H2O}))$$

and $$F(Y_1) = \frac{Y_1^{0.5}(1-Y_1)^{1.0}}{0.3849}$$

$F(T_1) = \mathrm{EXP}\,(-(13735/R)(1/T - 1/573.1))$ $F(P_{H2O}) = 1/1 + 3.803(P_{H2O})(\mathrm{EXp}(4968/R)(1/T - 1/573.1))$ wherein $Y_1$ is the fraction Co$_3$O$_4$ reduced t is the reduction time in minutes $A_1$ is the pre-exponential for reaction (1) for a 12.15% Co catalyst and equals 0.62

$F(Y_1)$ is the effect of extent of reduction on the reduction rate $F(T_1)$ is the effect of temperature on the reduction rate T is the absolute temperature in °K R is the gas constant, 1.987

$F(PH_2)$ is the effect of hydrogen partial pressure on reduction rate and is the hydrogen partial pressure in atm $F(PH_2O)$ is the effect of water partial pressure on the reduction rate Now, for the reaction CoO to metallic cobalt the kinetic expression is $$\frac{d(Y_2)}{dt} = (A_2)(F(Y_2))(F(T_2))(F(P_{H2}))(F(PH2O))$$

wherein
  $Y_2$ is the fraction of metallic cobalt that has formed;
  $A_2$ is the pre-exponential factor for the 12.15% catalyst and is 0.13
  $F(Y_2)$ is the effect of the extent of formation of metallic cobalt on the formation rate and is $(Y_2)^{.7}(Y_1-Y_2)^{2.0}/0.2133$
  $F(T_2)$ is the effect of temperature on the reduction rate and is $EXP((-18355/R)(1/T-1/573.1))$
  T and R are as previously described
  $F(P_{H2})$ is the effect of hydrogen partial pressure on the reduction rate and is the hydrogen partial pressure in atm
  $F(PH_2O)$ is the effect of water partial pressure on the reduction rate and is $$\frac{1 - PH_2O/(14.344)(PH_2)(EXP(1086/T))}{1 + 3.803(PH_2O)(EXP(4968/R)(1/T - 1/573.1))}$$

and $t_2$ is the reduction time in minutes

These rate expressions were developed with titania supported catalysts using thermogravimetric analysis techniques, and similar expressions were developed for alumina supported catalysts.

The kinetic model for the cobalt activation was developed from thermogravimetric analysis (TGA) data in which weights of the catalyst were measured periodically during reductions carried out at constant temperature. These weight data were then differentiated to obtain the rate of weight loss with time which is related to the reduction rate. Such isothermal data were obtained over a range of temperatures and reducing gas compositions (hydrogen, argon, and water vapor) to obtain measures of the effects of these variables on the reduction rate. Interpretation of the TGA data to develop the reduction model followed principles proposed by Brown and Galwey (Brown, Michael E., and Andrew K. Galwey). "Arrhenius Parameters for Solid-State Reactions from Isothermal Rate-Time Curves." Analytical Chemistry, Vol. 61, No. 10, May 15, 1989, pp. 1136-1139).

In a typical TGA experiment, approximately 0.1 mg of the titania-supported cobalt catalyst was charged to the balance pan of a Mettler Model TA-1 balance. Under a flow of 10 liters/minute of deoxygenated argon, the sample was heated to 500° C. and held at this temperature until constant weight was achieved to remove adsorbed moisture. The temperature was then lowered to a base temperature of 50° C. to obtain the weight loss by drying. Next, the sample was reheated in argon to the temperature at which the reduction experiment was to be conducted. At this temperature, reducing gas of the desired composition was introduced and the argon flow stopped. The reducing cycle was continued until constant weight was achieved, after which temperature was again lowered to the base temperature to determine the exact weight loss due to reduction that had occurred. To validate the experiment by assuring that no material had been blown from the balance pan, the weight of the catalyst after re-oxidation at 500° C. was compared with the original weight of the dried catalyst.

The weight data from the TGA experiment were downloaded to a spreadsheet program in which the derivative, or rate, data were calculated using the numerical techniques developed by Savitzky and Golay (Savitzky, Abraham and Marcel J. E. Golay. "Smoothing and Differentiation of Data by Simplified Least Squares Procedures." Analytical Chemistry, Vol. 36, No. 8, July 1964, pp. 1627-1639). The derivative curve calculated from the TGA data using the Savitzky-Golay procedure is shown in FIG. 4.

Figure 4:
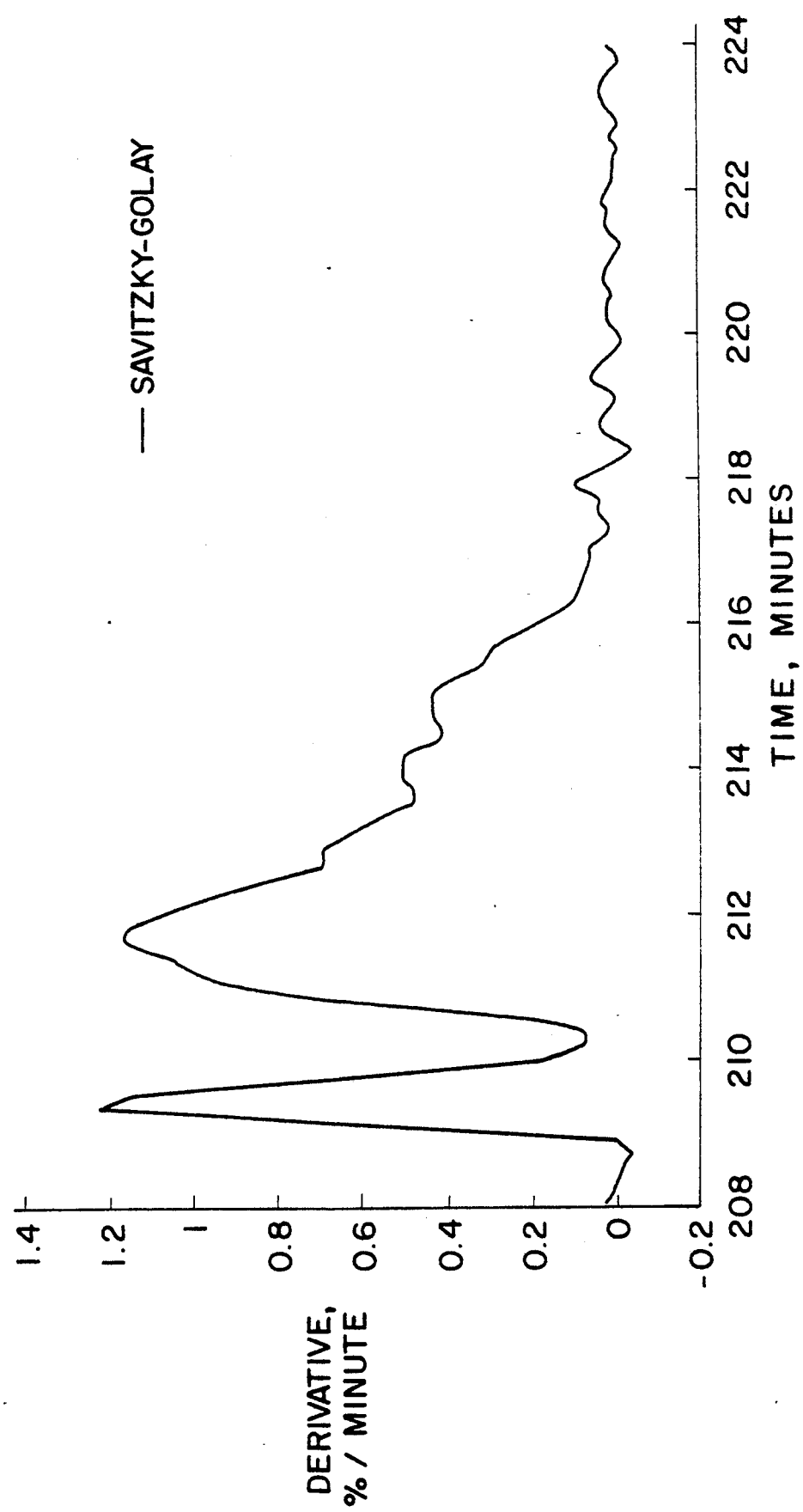
FIG. 4 shows a derivative curve calculated for thermogravimetric analysis data using a Savitsky-Golay procedure.

The derivative curve in FIG. 4 clearly shows two reduction peaks. The first corresponds to the reduction of $Co_3O_4$ to CoO while the second corresponds to the reduction of CoO to metallic cobalt. The dual peaks suggest that consecutive reactions are occurring and that the first reaction is nearly complete before the second reaction begins. The valley between the two peaks occurred after about one-fourth of the weight loss occurred, which also substantiates the concept of sequential reduction reactions. When reduction conditions of time and temperature were severe enough, the weight lost in the reduction agreed well with that expected if all of the $Co_3O_4$ were reduced to metallic cobalt.

Using the concepts of Brown and Galwey to interpret the nature of the reduction kinetics, the symmetry of each of the curves signals a sigmoid kinetic model rather than a deceleratory model. For a sigmoid kinetic model, the effect of the extent of reduction on the reduction rate can be represented mathematically by the following form:

$$F(y) = \frac{y^a * (1 - y)^b}{(a/(a + b))^a (b/(a + b))^b}$$

Figure 2B:
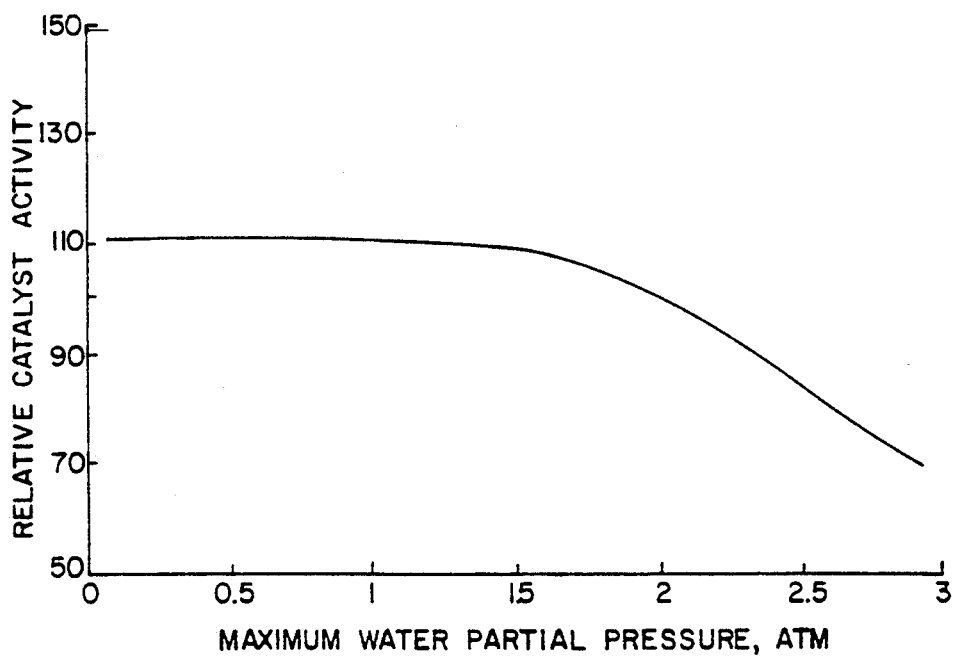
FIG. 2b is also a plot of relative catalyst activity at 190° C. v. maximum water partial pressure but concentrates on partial pressures up to 3 atmospheres, for Catalyst B, reduced in hydrogen with temperatures ramped from ambient to a maximum of 370°-400° C.

The coefficients a and b are chosen to fit the shape of the reduction curves, and the denominator normalizes the F(y) expression so that its values range between 0 and 1. The values at the peaks of the derivative curves in FIG. 2 are proportional to the rate constants for the two reduction reactions and can be correlated directly with the independent variables of temperature and reducing gas composition to develop the reduction model.

To summarize the procedure of developing such a reduction model, then, the following steps are used:
1) Obtain isothermal reduction rate data by TGA for the range of temperatures, pressures, and reducing gas compositions of interest and calculate the derivative curves
2) From the shapes of the derivative curves, select either the sigmoid or the deceleratory model as being more appropriate, and fit the appropriate mathematical form to the peaks
3) Correlate the maximum of the derivative curves with the independent operating variables to obtain a mathematical relationship for their effects.
4) These factors, combined with the stoichiometry of the reaction, can then be combined to obtain a comprehensive model of the reduction process.

The procedures described herein can be used, and modified as may be necessary, to determining water partial pressure effects for supports other than titania and reductions where water will be formed from the compound being reduced.

The following examples serve to illustrate this invention.

Two Co—Re—$TiO_2$ catalysts were prepared by impregnating an aqueous solution of cobalt nitrate and perrhenic acid onto titania extrudates. The extrudates contained about 3.5% alumina binder. Final calcination to decompose the nitrate salt was done in forced air ovens at 250° C. Catalyst extrudates were then ground and sized to 60-150 mesh for the activity tests and 60-100 mesh for the thermogravimetric (TGA) tests. The two catalysts differed in metal loading, as follows:

|  | Wt % Co | Wt % Re |
|---|---|---|
| Catalyst A | 6.85 | 0.64 |
| Catalyst B | 12.15 | 1.23 |

The higher cobalt loading was deposited in two impregnation/calcination steps.

Catalyst tests were made in a small fixed bed reactor. A 1.2 cc (1.66 g) charge of catalyst was diluted with 1.2 cc of titania (also 60-150 mesh) and tested in a reactor with a 0.245 inch ID. The reactor was heated in an infrared furnace which permitted rapid changes in temperature. Reductions were performed with pure hydrogen metered with a Brooks flow controller. Gas hourly space velocities refer to the flow rate measured at the back-end of the unit with a bubble tube. Activity data, shown in Tables 1 and 2, correspond to performance at 18-22 hours on feed at 280 psig with a 64H2-32CO-4Ne feed composition. Run temperature was 200° C. for Catalyst A and 190° C. for Catalyst B. The rate constant k shown in the tables is calculated from the following equation:

$$k = (GHSV/P) \ln\{1/(1-X)\}$$

where
GHSV = vol gas flow (@1 atm and room temperature) per hour per vol of catalyst only
P = pressure in atm = 20
X = fraction CO conversion Water was added during reduction via a metal saturator or a Ruska pump. Levels shown in Tables 1 and 2 correspond to calculated values. Direct measurement by Drager tube was unsuccessful because of condensation in the exit line during water addition.

Water concentration in the exit gas during reduction was not routinely measured. However, measurements were made in one side-by-side comparison of the effect of flow rate alone. As shown in FIG. 1, quite different concentration vs. time curves were observed for 750 vs. 15,000 GHSV at 100 psig reduction pressure. Water was removed much more slowly with the lower flow rate. The high flow case is 67% more active than the low flow case (see Table I). Other data in Tables I and II confirm that reductions at elevated pressure and low flow show consistently lower activity. Data also indicate that this activity debit cannot be eliminated by air regeneration. Water added after reduction does not appear to be as harmful. Either dry hydrogen or an air regeneration reverse the effect of post-reduction water.

Results from Tables I and II, taken under conditions where water buildup was low, are illustrated graphically in FIG. 3. A maximum in activity occurs after reduction at about 370° C. Higher temperature reductions are especially poor. XPS results are included in FIG. 3. The ratio of the cobalt metal intensity to the Ti intensity shows a curve shaped like the activity curves. The negative effect of high temperature reduction appears reversible. Application of a 250° C. air treat to a 550° C. reduced sample restores high activity. This point is noted as the "X" on FIG. 3. XPS data indicate that the low activity encountered with reductions below about 315° C. is due to incomplete reduction of the cobalt oxide.

The kinetics of cobalt reduction on titania supported catalysts were developed from experiments in which the rate of weight loss during reduction was measured by thermogravimetric analysis (TGA). Kinetics for other supports can be determined by similar analyses. A Mettler Model TA-1 balance and the Omnitherm software data-handling package were used to make the kinetic measurements. The average particle size for the catalysts was 50 microns, and material smaller than 44 microns was removed by screening to minimize the error due to fines being blown from the sample holder. The range of conditions covered in the kinetic study were as follows:

| Temperature, °C. | 275-400 |
|---|---|
| Total Pressure, Atm | 1.0 |
| Hydrogen Partial Pressure, Atm | 0.19-1.0 |
| Water Partial Pressure, Atm | 0.0-0.29 |
| Gas Flow Rate, L/Minute | 5.0-10.0 |
| Catalyst Cobalt Content, % | 2.5-14.0 |

The reduction of the cobalt oxide to metallic cobalt was found to occur in two sequential steps. In the first step, $Co_3O_4$ was reduced to CoO; in the second step, CoO was reduced to metallic cobalt. For each of the two steps, the reduction rate was autocatalytic in nature, i.e., the initial rate was low, then increased as reduction took place to a maximum value before falling off again as reduction for that step neared completion. The reduction rate increased with temperature, was first order in both hydrogen partial pressure and in the initial cobalt content of the catalyst, and was inhibited by the presence of water vapor. Large amounts of water vapor could also cause an equilibrium limitation of the second reaction.

TABLE I

| | Catalyst A | | | | | | | | |
|---|---|---|---|---|---|---|---|---|---|
| | Activation Conditions* | | | | | 200° C. Run Data | | | |
| Run No. | Temp °C. | P, psig | GHSV | Time, hour | Comment | GHSV | % Co Conv | Mol % CH4 | k |
| 1 | 450 | 100 | 750 | 2 | | 1250 | 73 | 3.6 | 82 |
| 2 | 450 | 100 | 15000 | 1 | | 1750 | 79 | 4.5 | 137 |
| 3 | 450 | 100 | 750 | 2 | | 1250 | 80 | 3.4 | 100 |
| 4 | 450 | 100 | 15000 | 1 | | | | | |
| | 450 | 100 | 15000 | 1 | 6% H2O | 1250 | 80 | 4.6 | 100 |
| 5 | 450 | 100 | 15000 | 1 | | | | | |
| | 450 | 100 | 15000 | 4 | 4% H2O | 1750 | 74 | 4.6 | 118 |
| 6 | 450 | 100 | 15000 | 1 | | | | | |
| | 450 | 100 | 15000 | 1 | 23% H2O | | | | |
| | | | | | | 1000 | 74 | 3.8 | 67 |

TABLE I-continued

Catalyst A

| Run No. | Activation Conditions* | | | | | 200° C. Run Data | | | |
|---|---|---|---|---|---|---|---|---|---|
| | Temp °C. | P, psig | GHSV | Time, hour | Comment | GHSV | % Co Conv | Mol % CH$_4$ | k |
| 7 | 450 | 100 | 15000 | 1 | | | | | |
|   | 450 | 100 | 15000 | 0.25 | 23% H$_2$O | | | | |
|   | 450 | 100 | 15000 | 1 | | 1400 | 67 | 4.0 | 78 |
| 8 | 450 | 100 | 15000 | 1 | | | | | |
|   | 450 | 100 | 3900 | 1 | 23% H$_2$O | | | | |
|   | 450 | 100 | 15000 | 1 | | | | | |
|   | 250 | 0 | 4000 | 1 | 5% O$_2$/N$_2$ | | | | |
|   | 450 | 0 | 5000 | 1 | | 1750 | 74 | 3.9 | 118 |
| 9 | 450 | 100 | 750 | 2 | | 1250 | 74 | 3.5 | 84 |
| 10 | 450 | 100 | 750 | 2 | | | | | |
|    | 450 | 100 | 15000 | 1 | | 1500 | 72 | 3.6 | 95 |
| 11 | 450 | 0 | 3000 | 1 | | | | | |
|    | 450 | 0 | 3900 | 1 | 23% H$_2$O | | | | |
|    | 250 | 0 | 4000 | 1 | 5% O$_2$/N$_2$ | | | | |
|    | 450 | 0 | 5000 | 1 | | 1750 | 75 | 3.9 | 121 |
| 12 | 450 | 100 | 750 | 2 | | | | | |
|    | 250 | 0 | 4000 | 1 | 5% O$_2$/N$_2$ | | | | |
|    | 450 | 0 | 5000 | 1 | | 1750 | 67 | 4.2 | 97 |
| 13 | 550 | 0 | 5000 | 1 | | 1500 | 74 | 4.4 | 101 |
| 14 | 450 | 200 | 750 | 2 | | 1000 | 74 | 3.5 | 67 |
| 15 | 371 | 0 | 5000 | 1 | | 2250 | 69 | 5.1 | 132 |
| 16 | 450 | 300 | 750 | 2 | | 1250 | 71 | 4.0 | 77 |

*Heat-Up Rate = 20° C./Minute

TABLE II

Catalyst B

| Run No. | Activation Conditions | | | | | | 190° C. Run Data | | | |
|---|---|---|---|---|---|---|---|---|---|---|
| | Heat-Up °C./Min. | Temp °C. | P, psig | GHSV | Time, hour | Comment | GHSV | % Co Conv | Mol % CH$_4$ | k |
| 1 | 20 | 371 | 35 | 300 | 1 | | 1250 | 68 | 3.1 | 71 |
| 2 | 20 | 371 | 35 | 300 | 4 | | 1500 | 72 | 3.0 | 95 |
| 3 | 20 | 400 | 0 | 5000 | 1 | | 1875 | 70 | 4.5 | 113 |
| 4 | 20 | 375 | 0 | 5000 | 1 | | 1875 | 70 | 4.8 | 113 |
| 5 | 1.67 | 375 | 35 | 300 | 3.5 | | 1500 | 80 | 3.3 | 121 |
| 6 | 1.67 | 375 | 35 | 1200/750 | 2 | | 1875 | 70 | 4.5 | 113 |
| 7 | 1.67 | 375 | 35 | 1200/750 | 2 | 5% H$_2$O | 1500 | 76 | 3.4 | 107 |
| 8 | 1.67 | 375 | 35 | 1200/750 | 2 | 6% H$_2$O | 2000 | 71 | 3.6 | 124 |
| 9 | 20 | 450 | 0 | 5000 | 1 | | 1500 | 75 | 4.3 | 104 |
| 10 | 20 | 500 | 0 | 5000 | 1 | | 1250 | 75 | 4.2 | 87 |
| 11 | 20 | 550 | 0 | 5000 | 1 | | 1250 | 71 | 4.2 | 77 |
| 12 | 20 | 300 | 0 | 5000 | 1 | | 1500 | 76 | 5.6 | 107 |
| 13 | 20 | 250 | 0 | 5000 | 1 | | 500 | 64 | 3.9 | 26 |
| 14 | 20 | 275 | 0 | 5000 | 1 | | 1500 | 74 | 4.4 | 101 |
| 15 | 20 | 550 | 0 | 1000 | 1 | | | | | |
|    | | 250 | 0 | 4000 | 3 | 5% O$_2$/N$_2$ | | | | |
|    | 20 | 375 | 0 | 5000 | 1 | | 1750 | 70 | 4.2 | 105 |

What is claimed is:

1. A method for preparing a cobalt containing hydrocarbon synthesis catalyst comprising
   (a) preparing a supported catalyst precursor containing cobalt oxide and capable of producing water when treated with hydrogen at reducing conditions,
   (b) substantially reducing the cobalt oxide at elevated pressures and temperatures with a hydrogen containing gas, and
   (c) maintaining the water partial pressure during step (b) at 0.1-5 atmospheres.

2. The method of claim 1 wherein the total pressure during step (b) is above about 1.3-10 atmospheres.

3. The method of claim 1 wherein the temperature during step (b) is about 250°-425° C.

4. The method of claim 1 wherein the relative activity of the catalyst is at least about 75% of the maximum attainable catalyst activity for a particular catalyst composition.

5. The method of claim 1 wherein the support surface area is less than 100 m$^2$/g.

6. The method of claim 1 wherein the support is a Group IVB metal oxide.

7. A method for preparing a high activity, cobalt-containing hydrocarbon synthesis catalyst which comprises:
   (a) preparing a supported cobalt catalyst precursor containing a cobalt oxide capable of producing water when treated with hydrogen at reducing conditions,
   (b) substantially reducing the cobalt oxide to its catalytically active form with a hydrogen containing gas at temperatures of about 250°-250° C. and total pressures of about 1.3-10 atmospheres, and
   (c) maintaining the water partial pressure during step (b) at about 0.1-2.0 atmospheres.

8. The method of claim 7 wherein the support is a Group IVB oxide having a surface area of less than about 100 m$^2$/g.

9. The method of claim 7 wherein a promoter is present on the catalyst precursor.

10. The method of claim 9 wherein the promoter is rhenium.

11. A method for preparing a cobalt-containing hydrocarbon synthesis catalyst comprising a supported cobalt catalyst precursor containing a cobalt oxide capable of forming water when treated with a hydrogen containing gas at reducing conditions, which comprising determining a maximum water pressure of about 0.1 to 5 atmospheres during the reducing step by relating total pressure, hydrogen and water concentrations in the reducing gas, total gas rate, rate of temperature increase, reactor type, and cobalt oxide concentration.

12. The method of claim 11 wherein the support is a Group IVB metal oxide with a surface area of less than 100 m²/g.

13. The method of claim 1 wherein the catalyst precursor is prepared by impregnating the support with a water soluble cobalt salt followed by treating with an oxygen containing gas and converting substantially all of the salt to the oxide.

14. The method of claim 7 wherein the catalyst precursor is prepared by impregnating the support with a water soluble cobalt salt followed by treating with an oxygen containing gas at 150–550° C. and converting substantially all of the salt to the oxide.

15. The method of claim 14 wherein the water partial pressure is about 0.1–2.0 atmospheres.

* * * * *